(12) United States Patent
Baaijens

(10) Patent No.: US 9,566,176 B2
(45) Date of Patent: *Feb. 14, 2017

(54) PREFORM PRODUCED BY ELECTROSPINNING, METHOD FOR PRODUCING THE SAME AND USE OF SUCH A PREFORM

(71) Applicant: Technische Universiteit Eindhoven, Eindhoven (NL)

(72) Inventor: Franciscus Petrus Thomas Baaijens, Eindhoven (NL)

(73) Assignee: Technische Universiteit Eindhoven, Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/047,348

(22) Filed: Feb. 18, 2016

(65) Prior Publication Data

US 2016/0220398 A1 Aug. 4, 2016

Related U.S. Application Data

(63) Continuation of application No. 13/943,925, filed on Jul. 17, 2013, now Pat. No. 9,272,076, which is a continuation of application No. 11/587,641, filed as application No. PCT/NL2005/000324 on Apr. 28, 2005, now Pat. No. 8,551,778.

(51) Int. Cl.

| | |
|---|---|
| *A61F 2/86* | (2013.01) |
| *A61B 17/11* | (2006.01) |
| *A61F 2/24* | (2006.01) |
| *D04H 1/42* | (2012.01) |
| *D04H 1/728* | (2012.01) |
| *D04H 13/00* | (2006.01) |
| *A61F 2/07* | (2013.01) |
| *A61L 31/14* | (2006.01) |
| *D04H 1/4374* | (2012.01) |

(52) U.S. Cl.
CPC .............. *A61F 2/86* (2013.01); *A61B 17/11* (2013.01); *A61F 2/07* (2013.01); *A61F 2/24* (2013.01); *A61F 2/2415* (2013.01); *A61L 31/148* (2013.01); *D04H 1/42* (2013.01); *D04H 1/4374* (2013.01); *D04H 1/728* (2013.01); *D04H 13/00* (2013.01); *A61B 2017/1107* (2013.01); *A61B 2017/1132* (2013.01); *A61B 2017/1135* (2013.01); *A61F 2230/0069* (2013.01)

(58) Field of Classification Search
CPC ............. A61B 17/11; A61B 2017/1107; A61B 2017/1135; D04H 1/42; D04H 1/4374; D04H 13/00; D04H 1/728; A61F 2/2415; A61F 2/07; A61F 2/24; A61L 31/148
See application file for complete search history.

(56) References Cited

U.S. PATENT DOCUMENTS

| | | |
|---|---|---|
| 6,491,511 B1 | 12/2002 | Duran |
| 2002/0042128 A1 | 4/2002 | Bowlin |
| 2002/0173213 A1 | 11/2002 | Chu |

OTHER PUBLICATIONS

Cross et al. (1961) Evaluation of Pericardial Monocups as Aortic Valve Replacements. Annals of Surgery, Nov. 1961. pp. 811-817.
Kim et al. (2003) Control of degradation rate and hydrophilicity in electrospun non-woven poly (d,l-lactide) nanofiber scaffolds for biomedical applications. Biomaterials 24 (2003) 4977-4985.
Cacciola (2000) A synthetic ber-reinforced stentless heart valve. Journal of Biomechanics 33 (2000) 653-658.

*Primary Examiner* — Suzanne Ziska
(74) *Attorney, Agent, or Firm* — Lumen Patent Firm

(57) ABSTRACT

The invention relates to a method for producing a preform by means of an electrospinning process. The present invention also relates to the use of the present preform as a substrate for growing human or animal tissue thereon. The present invention furthermore relates to a method for growing human or animal tissue on a substrate, wherein the present preform is used as the substrate.

10 Claims, 4 Drawing Sheets

PREFORM PRODUCED BY ELECTROSPINNING, METHOD FOR PRODUCING THE SAME AND USE OF SUCH A PREFORM

CROSS-REFERENCE TO RELATED APPLICATIONS

This application is a continuation of U.S. patent application Ser. No. 13/943,925 filed Jul. 17, 2013, which is incorporated herein by reference.

U.S. patent application Ser. No. 13/943,925 filed Jul. 17, 2013 is a continuation of U.S. patent application Ser. No. 11/587,641 filed Aug. 22, 2007, which is incorporated by reference.

U.S. patent application Ser. No. 11/587,641 filed Aug. 22, 2007 is a 371 of PCT Patent Application PCT/NL2005/000324 filed Apr. 28, 2005.

PCT Patent Application PCT/NL2005/000324 filed Apr. 28, 2005 claims priority of NL Patent Application 1026076 filed Apr. 29, 2004.

FIELD OF THE INVENTION

The present invention relates to a method for producing a preform by means of an electrospinning process. The present invention also relates to the use of a preform obtained in accordance with the present method, as well as to a method for growing human or animal tissue on a substrate.

BACKGROUND OF THE INVENTION

U.S. patent application No. 2002/0173213 discloses a biologically decomposable or absorbable fibre-like object produced by electrospinning. Such a method can only be used for producing substantially flat objects, such as membranes, whereas it is precisely three-dimensional preforms produced by electrospinning that are in great demand.

Consequently it is an object of the present invention to provide a method for producing a preform by electrospinning, from which preform three-dimensional objects can be made.

Another object of the present invention is to provide a preform that can be used as a substrate for growing human or animal tissue thereon.

Yet another object of the present invention is to provide a substrate for an artificial implant, in particular for a heart valve or a T-connection for blood vessels.

SUMMARY OF THE INVENTION

One or more of the above objects can be accomplished by using the method as referred to in the preamble, which is characterized by the following steps:
a) providing a mould made up of at least two submoulds, which submoulds substantially exclusively comprise convex surfaces;
b) applying at least one fibre layer to the surface of at least one of the submoulds of step a) by electrospinning;
c) combining at least one submould of step a) and at least one submould of step b);
d) applying at least one fibre layer to the surface of the assembly of step c) by electrospinning to obtain the preform.

The advantage of the present method is that it is possible to obtain a preform having any desired three-dimensional shape, using an electrospinning process, by converting the intended three-dimensional shape into a mould, which mould is subdivided into a number of submoulds. Said submoulds have a spatial configuration such that, besides the usual flat parts, they substantially exclusively comprise convex surfaces.

The present inventors have found that when a fibre layer is applied to a target having a complex three-dimensional shape, viz. convex, concave and flat parts, by means of an electrospinning process, problems occur in the forming of the fibre layer, since it appears not be possible to form a uniform fibre layer because extra fibres are formed between the concave edges of the mould. Thus it is difficult to provide such concave surfaces with a uniform fibre layer, which uniform fibre layer is highly desirable in practice.

The aforesaid problem has been solved by the steps a)-d) of the present method, in which the very presence of concave surfaces is avoided by subdividing the mould into a number of submoulds, which submoulds are so constructed that the submoulds do not have any concave shapes any more but substantially exclusively comprise convex surfaces besides the usual flat parts.

The various submoulds of which the mould is built up are so constructed that they can be combined to form the mould. The submoulds have one or more surfaces that are contiguous to one or ore surfaces of the other submoulds, so that said submoulds fit together so as to jointly form the mould.

Since the preforms that are used in practice frequently have concave as well as convex surfaces, it has not been possible so far to produce such complex three-dimensional preforms provided with a uniform fibre layer by coating the mould by means of an electrospinning process.

The present inventors have found, however, that it is possible to obtain the desired preforms by subdividing the mould into a number of submoulds, which submoulds each mainly comprise convex surfaces besides the usual flat parts that are already present. Subsequently, said submoulds can be separately provided with fibre layers in one or more steps, after which the submoulds provided with fibre layers can be joined together and as a whole be provided with an additional fibre layer so as to strengthen the whole.

The submoulds are made of a material that is suitable for use with electrospinning, such as a metal. Also other suitable materials can be used, however.

The submoulds may be solid or partially hollow. If the submoulds are partially hollow, they may have a closed exterior surface. The submoulds or the mould may be provided with one or more openings, in which openings holders can be fitted, for example, which holders can be used for correctly positioning the submoulds or the mould during the electrospinning process.

The fibre layer(s) is(are) applied to the surface of the submould/mould, which surface is understood to be the exterior surface of the submould/mould. It is preferred to provide a large part of the submould/mould with at least one fibre layer. It is also possible, however, to provide only part of the surface of the submould/mould with at least one fibre layer. Thus it is possible, for example, not to provide the part of the submould/mould that comprises the holder and/or the part that is used for positioning the submould/mould during the electrospinning process with at least one fibre layer.

In a specific embodiment of the present invention, at least two fibre layers are applied in step b), viz, first a fibre layer V and subsequently a fibre layer W, with the fibre layer V and the fibre layer W having mutually different biological decomposition rates. Said decomposition rate can be measured in accordance with standard methods, for example, which methods will not be explained in more detail herein.

Preferably, the biological decomposition of the fibre layer V takes place more rapidly than that of the fibre layer W. In this way the outer layer W of the common fibre layer provides the required strength, whilst the inner fibre layer V can be substituted for natural tissue.

According to another preferred embodiment, a fibre layer N is used in step b) and a fibre layer M is used in step d), with the fibre layer M being biologically decomposed more quickly than the fibre layer N. In this case, too, the fibre layer N functions to provide stability, whilst the fibre layer M, which is applied as the outer layer for keeping the individual fibre layers of the submoulds together, will decompose more rapidly.

In yet another embodiment of the present invention, more than two fibre layers are provided, which layers can all be individually selected from the fibre layers V, W, N and M.

Any fibre material that can be processed by electrospinning can be used as the material for the fibre layer. It is possible, for example, to use polymeric materials, in particular biologically compatible polymeric materials, as the fibre material.

Another especially preferred embodiment relates to the use of a fibre layer comprising fibres composed of at least two components, wherein the various components have mutually different biological decomposition rates. The fibre consists of sequentially arranged component a and component b, for example, so that a fibre exhibiting a repetitive composition -a-b-a-b-a-b- is obtained. When such a fibre layer is used, one of the two components will decompose after some time, so that a collection of short fibres remains, viz, the fibres of the component having the slower decomposition rate. The short fibres, which are still present, contribute to the mechanical strength of the newly formed natural tissue, whilst the tissue can grow, which is not possible when a fibre layer that only consists of a slowly decomposing component is produced.

An advantage of the use of a fibre layer consisting of fibres that are composed of two components is the fact that when a preform made of such fibres is used for implantation into young patients, no subsequent surgery is required for exchanging the implant for a larger implant. After all, the implant produced in accordance with the present invention can grow with the patient.

The present invention also relates to the use of a preform obtained with the present method as a substrate for growing human or animal tissue thereon. The fibre layer that has been applied by electrospinning is a porous network on which cells can grow.

Subsequently, the substrate with the cells that have grown thereon can be implanted at the intended position in the body. A number of preferred embodiments are defined in the subclaims and will be explained in more detail hereinafter.

The present invention furthermore relates to a method for growing human or animal tissue on a substrate, wherein the present preform is used as the substrate. In this way the preform obtained by electrospinning can be provided with a layer of human or animal tissue. Thus, an implant that can be used for implantation into a human or animal body can be obtained through incubation with human or animal cells. Such incubation can be carried out in a bioreactor, for example, in which a specific substrate solution is present, in which substrate solution the cells to be grown are present. Said incubation can be carried out under suitable conditions of temperature, time, pH and the like so as to optimise the cell growth. This will be explained in more detail hereinafter.

The present invention will now be explained in more detail by means of a description of a number of preferred embodiments, in which reference is made to the accompanying drawings. The present invention is not limited to such specific embodiments, however.

DETAILED DESCRIPTION

The present invention will now be explained in more detail with reference to the drawings, which show especially preferred embodiments of the present invention. A preform is made, among other things, which preform functions as a mould for a heart valve (FIGS. 1-3). The drawings show a mould for a heart valve comprising three membranes; according to the invention, however, also other types of valves comprising more or fewer membranes can be produced.

Figure 1A:
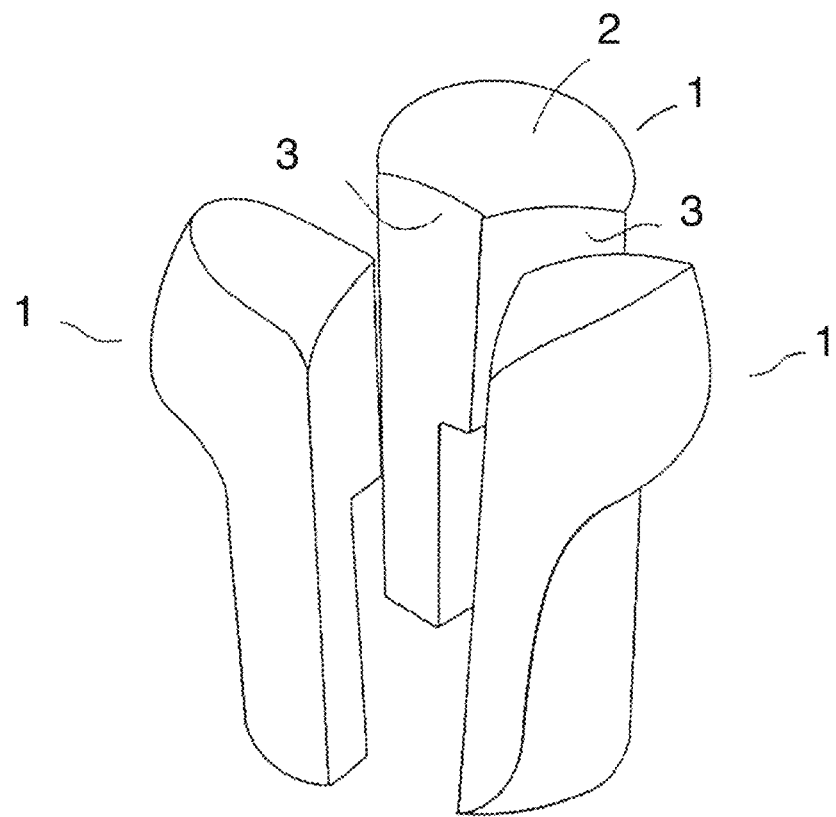
FIG. 1a shows three submoulds of a mould for an artificial, three-membrane heart valve.

FIG. 1a shows three submoulds 1, each comprising one upper surface 2 and two contact surfaces 3, which submoulds are each separately provided with a fibre layer by means of an electrospinning process. Said three submoulds 1 are so constructed that they substantially exclusively comprise convex surfaces besides the usual flat surfaces. It should be understood that the submould I does not have any concave surfaces, so that said electrospinning will lead to a uniform fibre layer. The submoulds 1 are configured to fit together to form the mould.

Figure 1B:
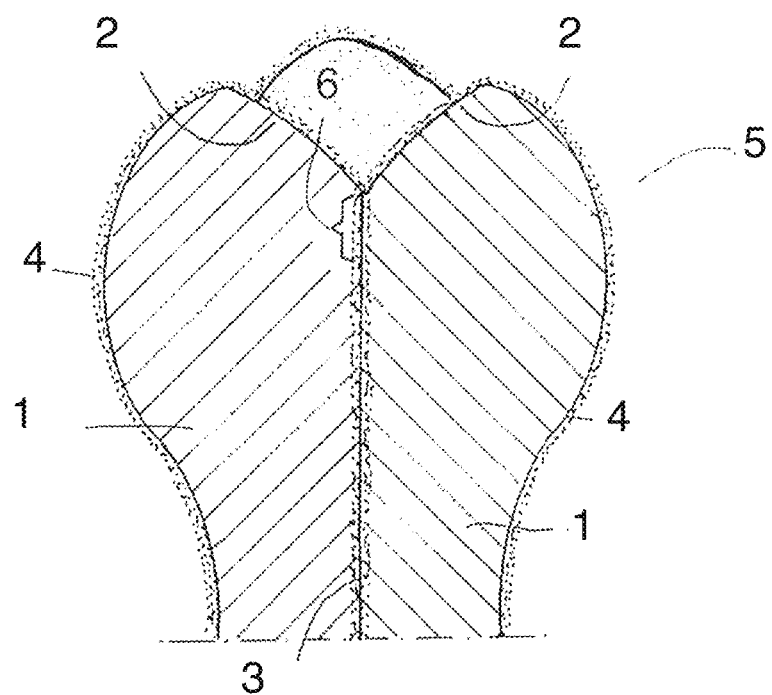
FIG. 1b is a sectional view of an assembly of the submoulds of FIG. 1a, which have been provided with a fibre layer by electrospinning.

FIG. 1b is a sectional view of the three submoulds 1 of FIG. 1a, showing the submoulds after a fibre layer 4 has been applied to each of the individual submoulds 1. The submoulds 1 have subsequently been combined into an assembly 5 by placing the contact surfaces 3 into abutment with each other. The part 6 is called the co-optation surface, which is very important in obtaining a properly functioning artificial heart valve. The fact is that such a co-optation surface ensures that the membranes will correctly butt together after the incubation of the preform with human or animal cells so as to obtain the final biological heart valve. Since a certain degree of shrinkage of the preform may occur during incubation, it is important that an extra edge (the co-optation surface) is present on the membranes, so that said co-optation surfaces 6 can prevent openings being formed between the membranes when shrinkage occurs, which openings might lead to a leaking heart valve. Such a co-optation surface is not obtained if a single mould for a heart valve is used instead of three submoulds 1 according to the present invention.

Figure 2A:
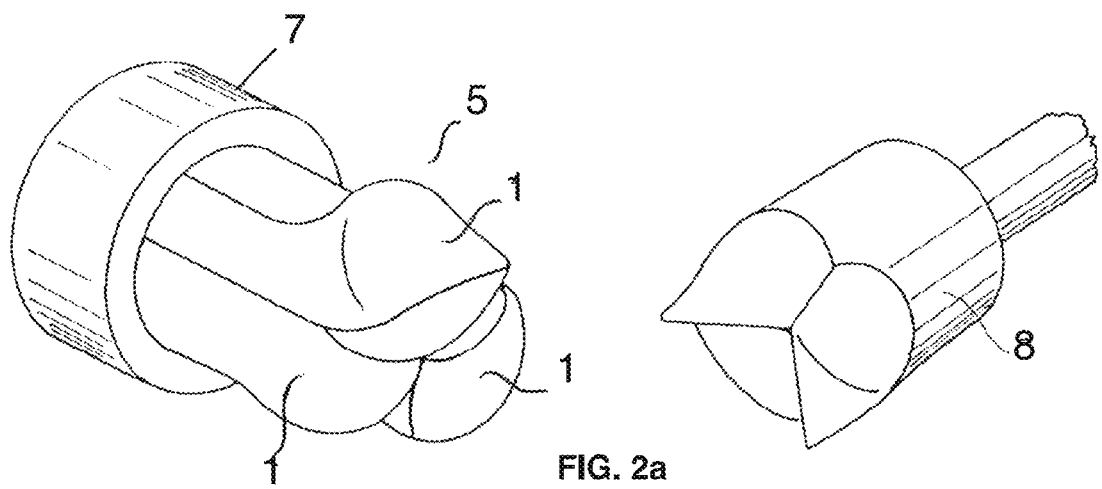
FIG. 2a shows an assembly of the three submoulds of FIG. 1a and a complementary submould for obtaining a complete heart valve, whilst

FIG. 2a shows the assembly 5 of the submoulds 1 provided with a fibre layer (not shown). The assembly 5 is held together by means of a ring construction 7, but it is also possible to use other, conventional methods, of course. Furthermore, a complementary submould 8 is shown, which can be placed on the end of the assembly 5 with a close and precise fit.

Figure 2B:
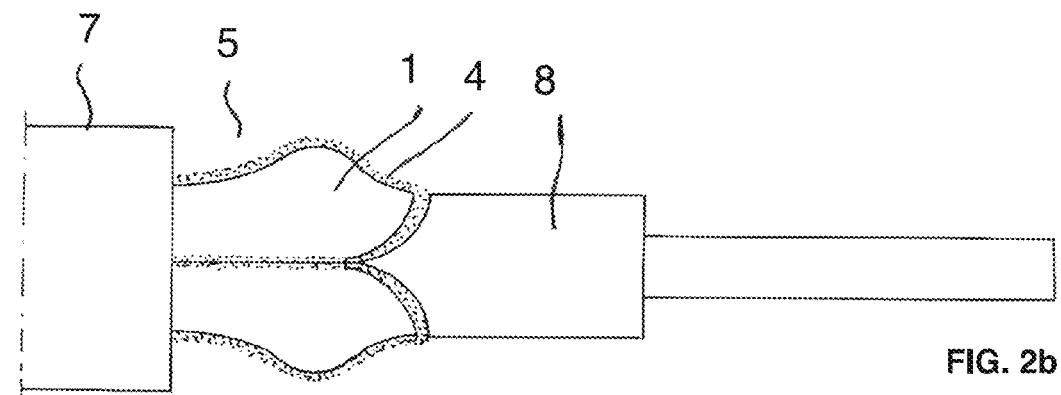
FIG. 2b is a sectional view of the submoulds of FIG. 2a slid one into another.

The entire mould of the heart valve as shown in FIG. 2b consists of the assembly 5 of three submoulds 1 provided with a fibre layer, a ring construction 7 and the submould 8. In a next step (d) of the method, the entire mould will be provided with a fibre layer 9 by electrospinning.

Figure 2C:
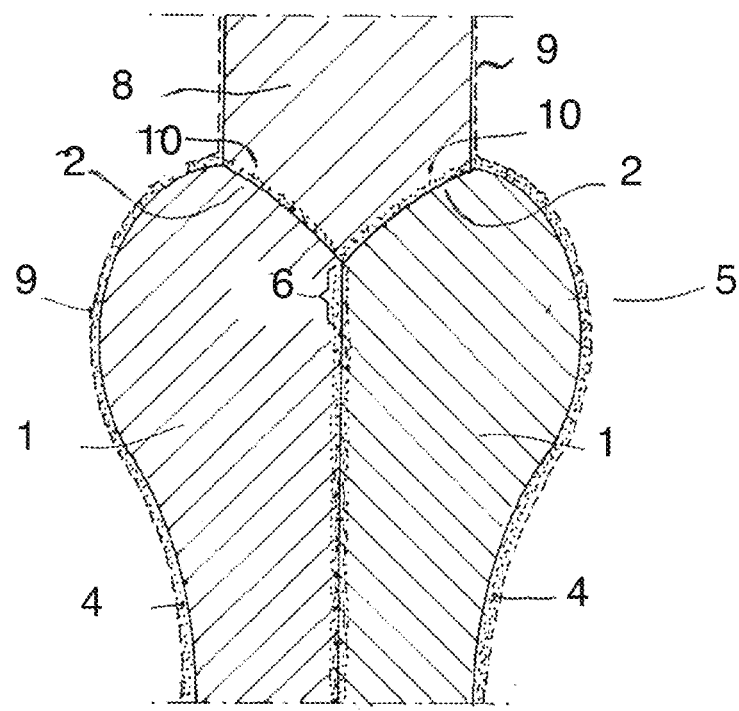
FIG. 2c is a sectional view of the entire mould for the heart valve comprising fibre layers obtained after electrospinning.

FIG. 2c is a sectional view of the mould after step d), showing submoulds 1,8 with upper surfaces 2 and fibre layers 4,9. The figure furthermore shows the co-optation surface 6, which forms part of the fibre layer 4, membranes 10, likewise forming part of the fibre layer 4, which membranes 10 are formed on the upper surfaces 2 of the submoulds 1.

Figure 3A:
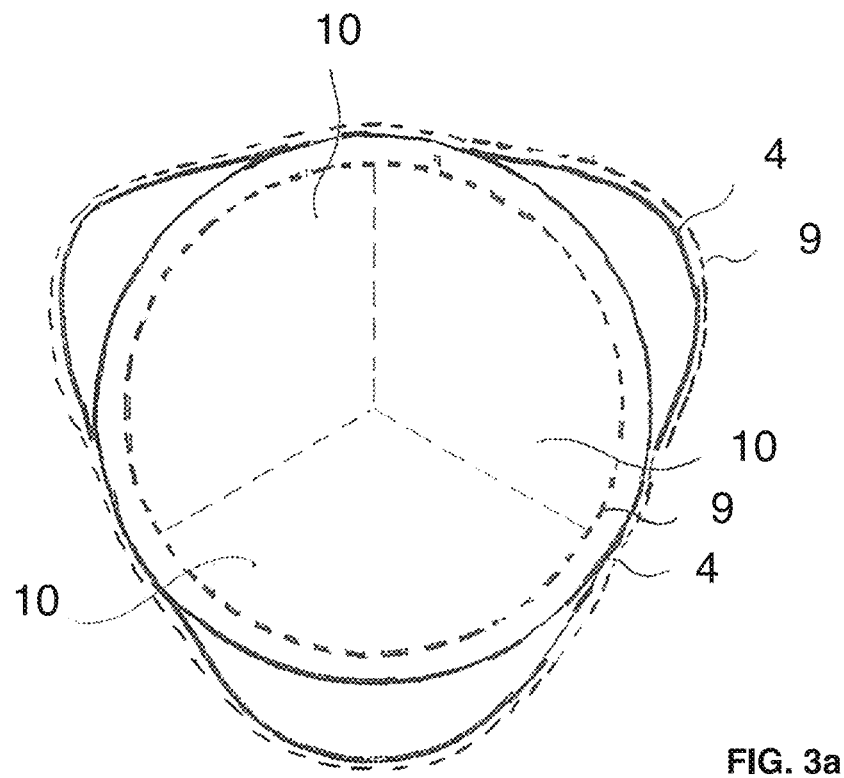
FIGS. 3a and 3b are a top plan view and a side view, respectively, of a preform according to the present invention obtained by using the mould of FIGS. 2a-2c.
Figure 3B:
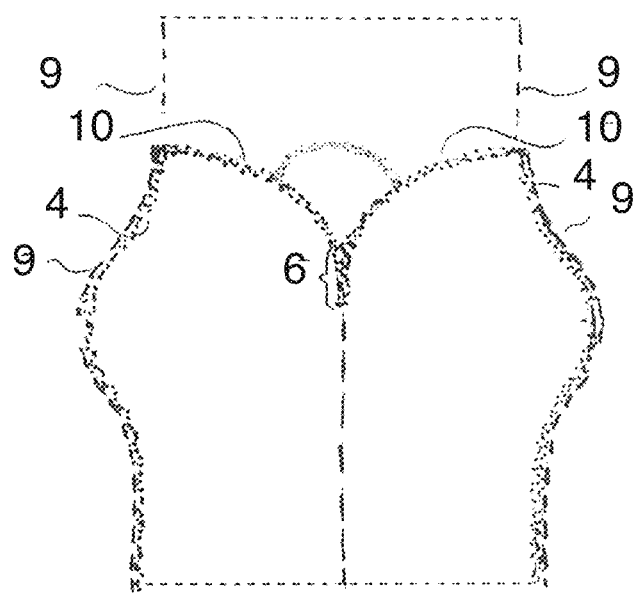

FIGS. 3a and 3b are views of the preform thus obtained after the submoulds 1,8 have been removed. Said submoulds can be carefully removed from the fibre layer(s) by one. Said removal may take place by hand, for example. In addition, part of the fibre layers 4 on the internal contact surfaces 3 is removed, with the exception of the co-optation surface 6, which is maintained. FIG. 3a is a top plan view and FIG. 3b is a side view of the preform after the submoulds 1,8 have been removed, showing the membranes 10, the fibre layer 4 (full line) and the fibre layer 9 (dotted line), whilst FIG. 3b also shows the co-optation surface 6.

Although the production of artificial heart valves has already been extensively described in the literature, with U.S. patent application No. 2002/0173213 disclosing the use of artificial heart valves made of metal alloys, such heart valves have this drawback that a material that does not naturally occur in the body (metal alloy) is implanted into the body, where it will permanently remain.

Consequently, the present invention has this advantage that a fibre-like preform in the form of a heart valve can be obtained, which preform comprises biologically decomposable components.

The obtained fibre-like preform according to the present invention can be incubated with human or animal cells, which are able to grow in the open fibre-like structure. To this end, the present fibre-like preform is transferred to a container in which a usual cell growth medium is present, to which human or animal cells are subsequently added. Then the whole is cultured for a specific period of time under standard culturing conditions. In this way an artificial implant based on the present fibre-like preform provided with human or animal tissue is obtained.

The implant thus obtained can be implanted into a human or animal body. There is a possibility that the preform will partially or entirely decompose during the culturing of human or animal tissue, but there is also a possibility of the decomposition of the preform continuing or starting after implantation. Thus it is preferable according to the invention to use a biologically decomposable or absorbable material for the preform, so that the preform will have decomposed substantially completely after some time and have been replaced by natural tissue, so that a fully natural implant will be present in the body, in contrast to the metal heart valves according to the prior art.

Another embodiment of the present invention relates to the use of the present preform as a substrate for connecting one or more blood vessels, as shown in FIG. 4. When one or more blood vessels are connected by suturing, leakage frequently occurs, because this is a complex procedure and the blood vessels are so small and circular in shape that suturing is problematic. Consequently, there is a need for a T-piece that can be used for connecting two or more blood vessels.

Figure 4A:
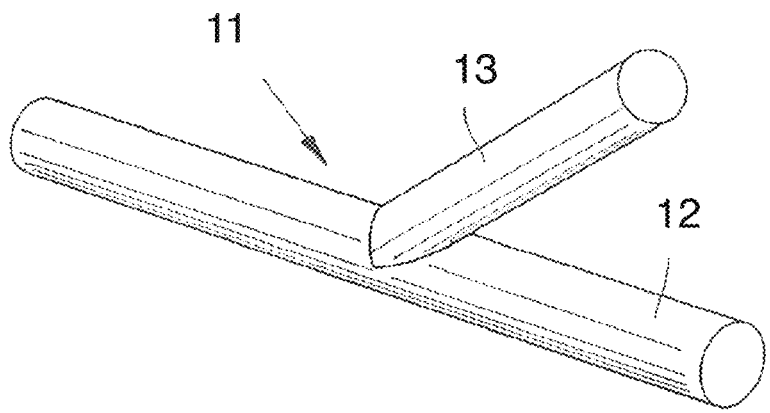
FIG. 4a shows a mould according to another embodiment of the present invention, a T-piece for connecting two or more blood vessels.

FIG. 4a shows a mould of a T-piece 11 provided with two branches 12,13 for joining two blood vessels.

Figure 4B:
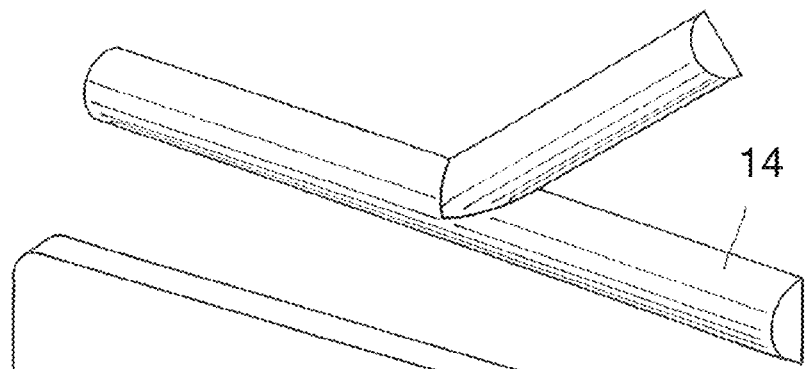
FIGS. 4b and 4c show two possible embodiments of a submould.

FIG. 4b shows a submould 14 which, in combination with the mirror image thereof (not shown), forms the complete mould for the T-piece. It should be understood that the submould 14 does not comprise any concave surfaces, so that the electrospinning process will provide a uniform fibre layer. The two submoulds 14 are separately provided with a fibre layer by electrospinning, and subsequently the two submoulds provided with the fibre layer are joined together, after which the submoulds thus joined together are bonded to each other, for example by means of tubes previously formed by electrospinning or by providing an extra fibre layer by electrospinning.

Figure 4C:
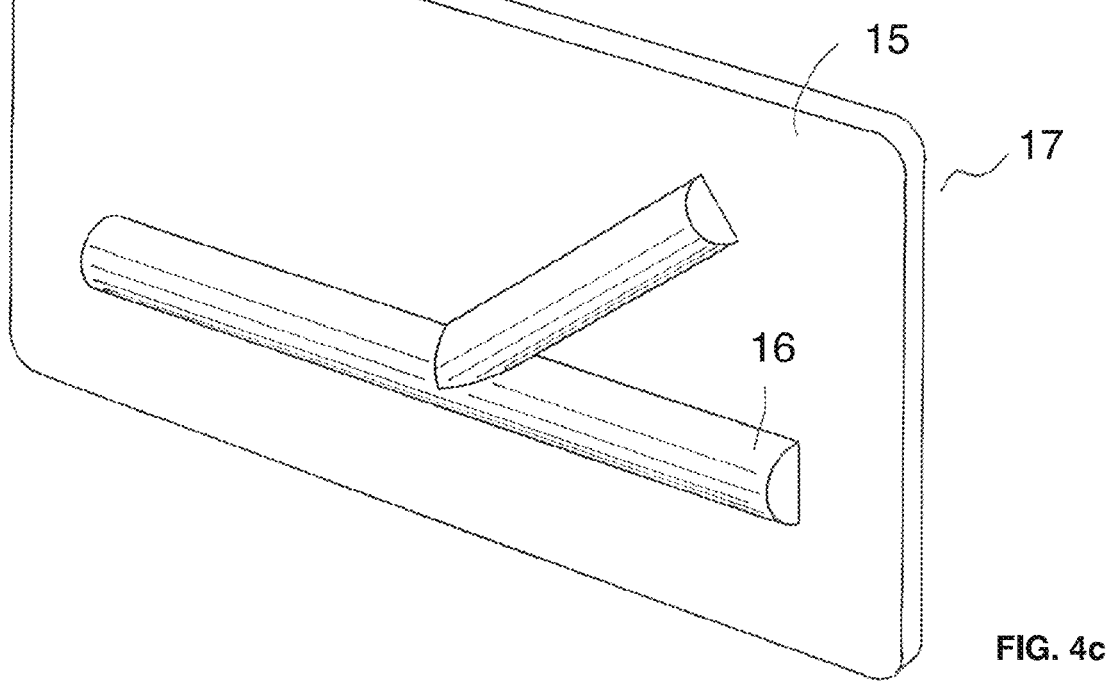

An alternative to the above geometry of the submould 14 is shown in FIG. 4c, in which the submould 17 consists of a flat plate 15 with the same geometric FIG. 16 as shown in FIG. 4b present thereon. This mould will provide a satisfactory distribution of the fibres. Once the fibre layer has been applied to the submould 17 according to FIG. 4c by electrospinning, the fibre layer can be removed from the plate 15 along the lines of the geometric FIG. 16, and subsequently the final mould as shown in FIG. 4a can be formed in the same manner as described above by bonding the fibre layers of the two submoulds together.

A preform for a T-connection 11 according to the invention obtained in this manner can be used for growing human or animal tissue thereon and be used for implantation in a comparable manner as described above with regard to heart valves.

Although the present invention has been explained on the basis of two preferred embodiments, it is also possible to use the present invention for producing other preforms to be used in the production of implants for other parts of the body, such as other valves in the heart or blood vessels, or parts of joints, for example a kneecap, and the like.

What is claimed is:

1. A method for implanting a tubular preform for connecting one or more blood vessels, comprising:
   providing an electrospun, porous, biodegradable tubular preform having membranes produced by electrospinning at least two fibre layers over submoulds, the tubular preform having an open fiber-like structure and the tubular preform having at least two branches for joining two blood vessels; and
   implanting the tubular preform in a human or animal body, wherein the tubular preform decomposes substantially completely and is replaced by natural tissue, and wherein the tubular preform forms at least part of a blood vessel.

2. The method as in claim 1, wherein the tubular preform is incubated with human or animal cells prior to incubation to allow cells to grow in the open fiber-like structure to provide tissue over the tubular preform.

3. The method as in claim 1, wherein the tubular preform at least partially degrades prior to implantation.

4. The method as in claim 1, wherein the tubular preform entirely degrades prior to implantation.

5. The method as in claim 1, wherein the two fibre layers have different decomposition rates.

6. A tubular preform for connecting one or more blood vessels, comprising:

an electrospun, porous, biodegradable tubular preform having membranes produced by electrospinning at least two fibre layers over submoulds, the tubular preform having an open fibre-like structure, the tubular preform having at least two branches for joining two blood vessels, and the tubular preform being configured to decompose substantially completely and be replaced by natural tissue after implantation into a human or animal body, and wherein the tubular preform forms at least part of a blood vessel.

7. The tubular preform as in claim 6, wherein the tubular preform is configured to allow human or animal tissue to grow in the open fibre-like structure as a result of incubation with human or animal cells prior to implantation.

8. The tubular reform as in claim 6, wherein the tubular preform is configured to at least partially degrade prior to implantation.

9. The tubular preform as in claim 6, wherein the tubular preform is configured to entirely degrade prior to implantation.

10. The tubular preform as in claim 6, wherein the two fibre layers have different decomposition rates.

\* \* \* \* \*